United States Patent [19]

Bryan et al.

[11] Patent Number: 5,674,296
[45] Date of Patent: Oct. 7, 1997

[54] HUMAN SPINAL DISC PROSTHESIS

[75] Inventors: Vincent Bryan, Mercer Island; Alex Kunzler, Bellevue, both of Wash.

[73] Assignee: Spinal Dynamics Corporation, Bellevue, Wash.

[21] Appl. No.: 681,230

[22] Filed: Jul. 22, 1996

Related U.S. Application Data

[63] Continuation-in-part of Ser. No. 339,490, Nov. 14, 1994, abandoned.

[51] Int. Cl.$^6$ ..................................................... A61F 2/44
[52] U.S. Cl. ................................................ 623/17; 606/61
[58] Field of Search ............................. 623/16–17, 18; 606/61, 72, 73

[56] References Cited

U.S. PATENT DOCUMENTS

| | | | |
|---|---|---|---|
| 2,677,369 | 5/1954 | Knowles | 606/61 |
| 4,599,086 | 7/1986 | Doty | 606/61 X |
| 4,911,718 | 3/1990 | Lee et al. | 623/17 |
| 4,932,969 | 6/1990 | Frey et al. | 623/17 |
| 4,997,432 | 3/1991 | Keller | 606/61 |
| 5,171,281 | 12/1992 | Parsons et al. | 623/17 |
| 5,192,326 | 3/1993 | Bao et al. | 623/17 |
| 5,370,697 | 12/1994 | Baumgartner | 623/17 |

FOREIGN PATENT DOCUMENTS

| | | | |
|---|---|---|---|
| 3023353 | 4/1981 | Germany | 623/17 |
| 895433 | 1/1982 | U.S.S.R. | 623/17 |
| 1560184 | 4/1990 | U.S.S.R. | 623/17 |

*Primary Examiner*—Mary Beth Jones
*Attorney, Agent, or Firm*—Gardner, Carton & Douglas

[57] ABSTRACT

The invention relates to a spinal disc endoprosthesis. The endoprosthesis has a resilient body formed of one or more materials which may vary in stiffness from a relatively stiff exterior annular gasket portion to a relatively supple central nucleus portion. Concaval-convex elements at least partly surround that nucleus portion so as to retain the nucleus portion and gasket between adjacent vertebral bodies in a patient's spine. Assemblies of endoprosthetic discs, endoprosthetic vertebral bodies, and endoprosthetic longitudinal ligaments may be constructed. To implant this endoprosthesis assembly, information is obtained regarding the size, shape, and nature of a patient's damaged spine. Thereafter, one or more prosthetic vertebral bodies and disc units are constructed in conformity with that information. Finally, the completed and conformed vertebral body and disc assembly is implanted in the patient's spine.

43 Claims, 5 Drawing Sheets

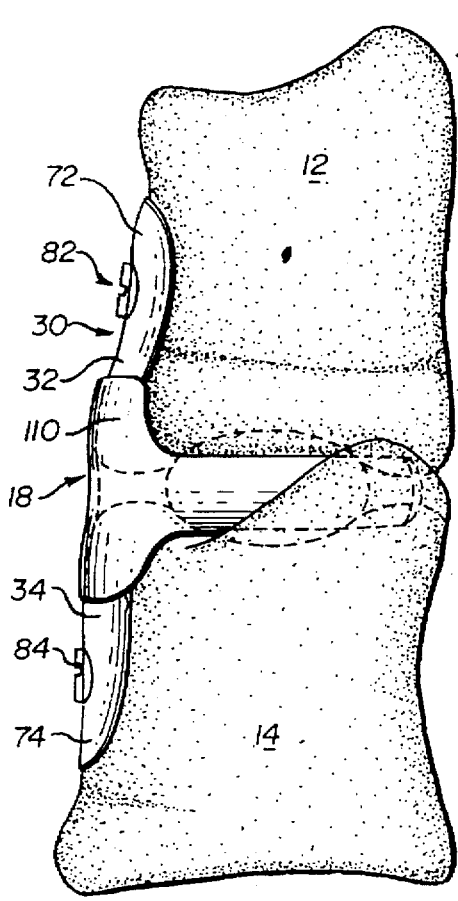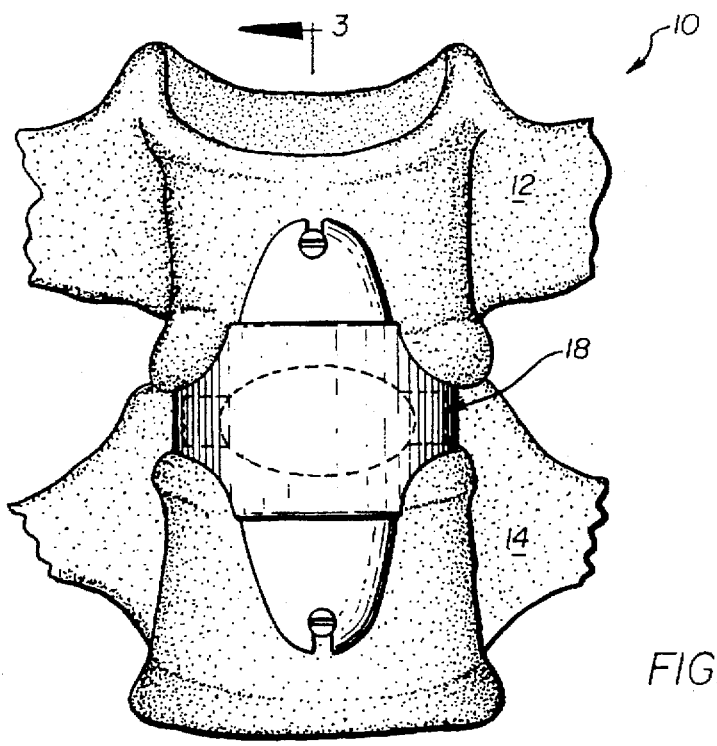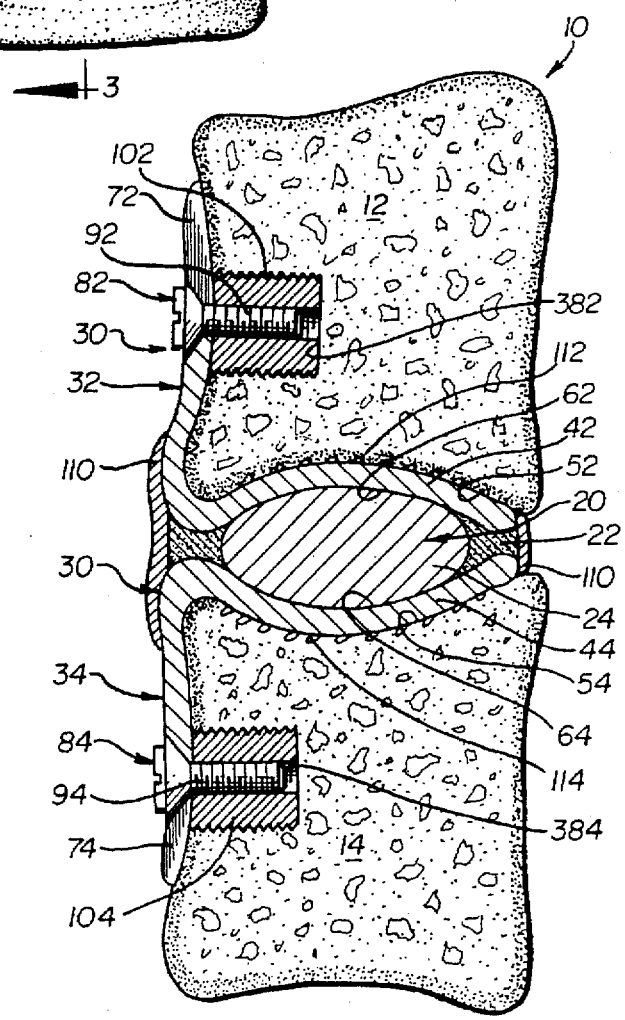

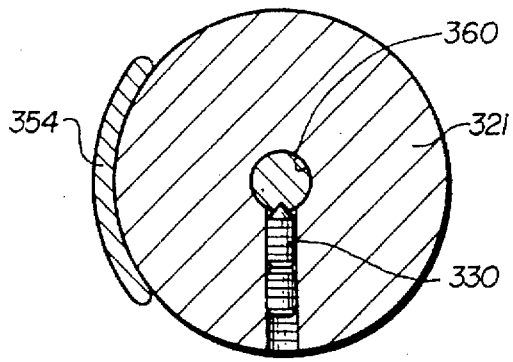
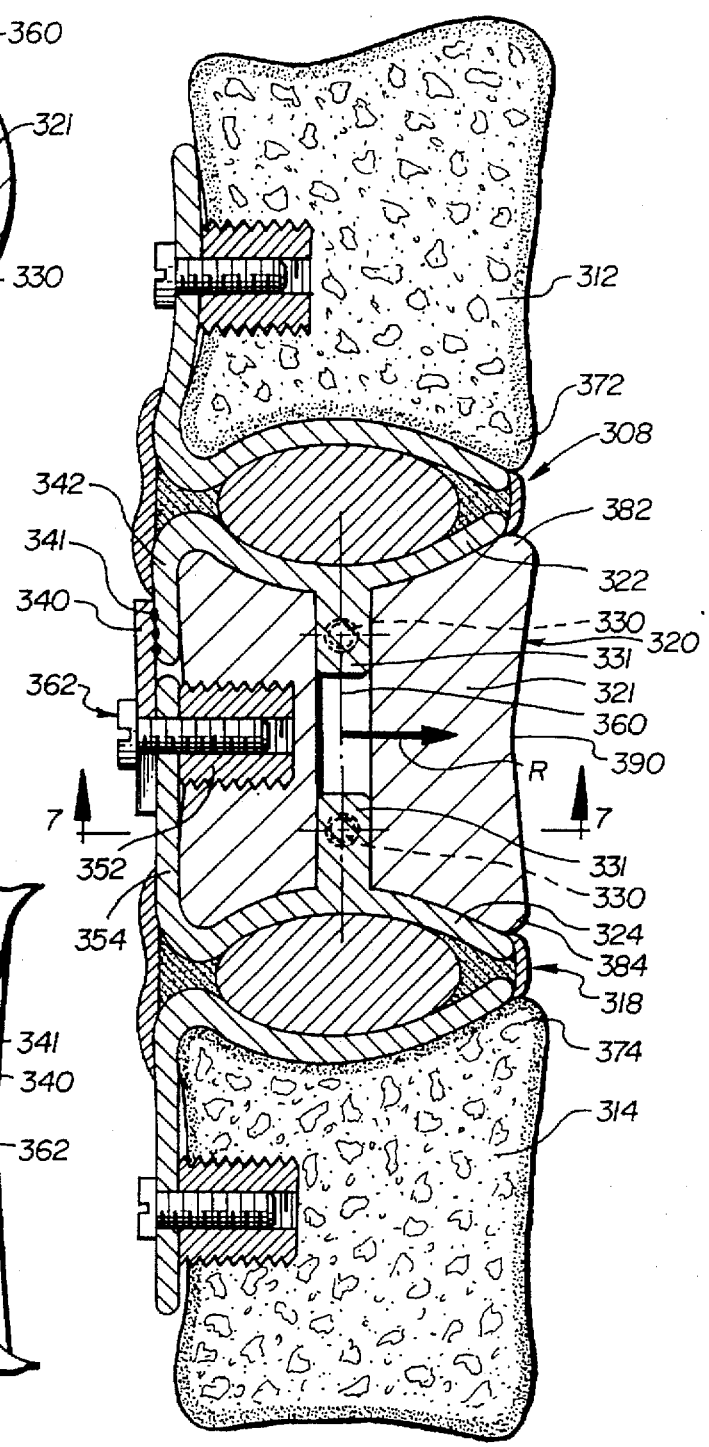
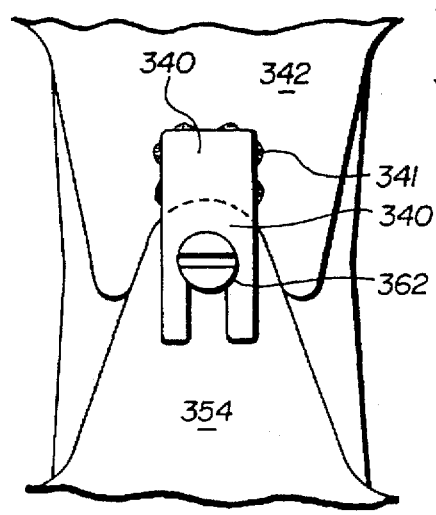

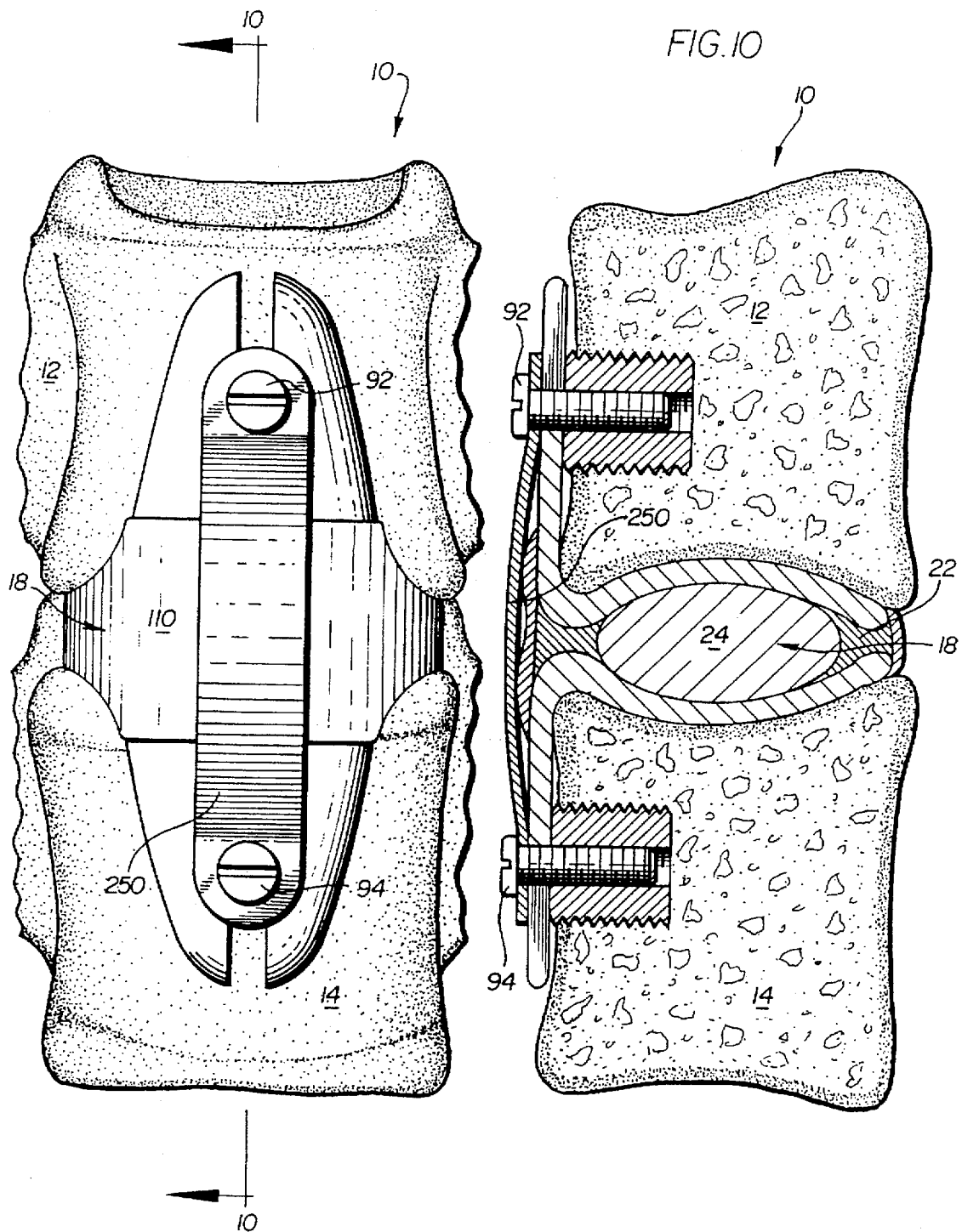

HUMAN SPINAL DISC PROSTHESIS

This is a continuation-in-part of U.S. patent application Ser. No. 08/339,490, filed Nov. 14, 1994, which is abandoned.

BACKGROUND OF THE INVENTION

This invention relates generally to human prostheses, and especially to spinal column vertebral disc prostheses. The invention also relates to surgical procedures for preparing the patient to receive a vertebral disc endoprosthesis, and for implanting that endoprosthesis in the patient's spine.

The herniation of a spinal disc and the often resultant symptoms of intractable pain, weakness, sensory loss, incontinence and progressive arthritis are among the most common of debilitating processes affecting mankind. If a patient's condition does not improve after conservative treatment, and if clear physical evidence of nerve root or spinal cord compression is apparent, and if correlating radiographic studies (i.e., MRI or CT imaging or myelography) confirm the condition, surgical removal of the herniated disc may be indicated. The process of discectomy—as the name implies—involves the simple removal of the disc without attempt to replace or repair the malfunctioning unit. In the United States in 1985, over 250,000 such operations were performed in the lumbar spine and in the cervical spine.

Statistics suggest that present surgical techniques are likely to result in short-term relief, but will not prevent the progressive deterioration of the patient's condition in the long run. Through better pre-operative procedures and diagnostic studies, long-term patient results have improved somewhat. But it has become clear that unless the removed disc is replaced or the spine is otherwise properly supported, further degeneration of the patient's condition will almost certainly occur.

In the mid-1950's and 60's, Cloward and Smith & Robinson popularized anterior surgical approaches to the cervical spine for the treatment of cervical degenerative disc disease and related disorders of the vertebrae, spinal cord and nerve root; these surgeries involved disc removal followed by interbody fusion with a bone graft. It was noted by Robinson (Robinson, R. A.: The Results of Anterior Interbody Fusion of the Cervical Spine, J. Bone Joint Surg., 440A: 1569-1586, 1962) that after surgical fusion, osteophyte (bone spur) reabsorption at the fused segment might take place. However, it has become increasingly apparent that unfused vertebral segments at the levels above and below the fused segment degenerate at accelerated rates as a direct result of this fusion. This has led some surgeons to perform discectomy alone, without fusion, by a posterior approach in the neck of some patients. However, as has occurred in surgeries involving the lower back where discectomy without fusion is more common as the initial treatment for disc herniation syndromes, progressive degeneration at the level of disc excision is the rule rather than the exception. Premature degenerative disc disease at the level above and below the excised disc can and does occur.

Spine surgery occasionally involves fusion of the spine segments. In addition to the problems created by disc herniation, traumatic, malignant, infectious and degenerative syndromes of the spine can be treated by fusion. Other procedures can include bone grafts and heavy duty metallic rods, hooks, plates and screws being appended to the patient's anatomy; often they are rigidly and internally fixed. None provide for a patient's return to near-normal functioning. Though these procedures may solve a short-term problem, they can cause other, longer term, problems.

A number of attempts have been made to solve some of the problems described above by providing a patient with spinal disc prostheses, or artificial discs of one sort or another. For example, Steffee, U.S. Pat. No. 5,031,437, describes a spinal disc prosthesis having upper and lower rigid flat plates and a flat elastomeric core sandwiched between the plates. Frey et al., U.S. Pat. Nos. 4,917,704 and 4,955,908, disclose intervertebral prostheses, but the prostheses are described as solid bodies.

U.S. Pat. Nos. 4,911,718 and 5,171,281 disclose resilient disc spacers, but no inter-connective or containing planes or like elements are suggested, and sealing the entire unit is not taught.

It is the primary aim of the present invention to provide a vertebral disc endoprosthesis which will perform effectively and efficiently within a patient's spine over a long period of time, and which will not encourage degeneration of or cause damage to adjacent natural disc parts.

It is another object to provide a vertebral disc endoprosthesis which does not require pins or other common mechanical hinge elements, yet which permits natural motion of the prosthetic parts and the adjacent natural anatomy.

It is a related objective to provide a new vertebral disc endoprosthesis surgical procedure which will decrease post-operative recovery time and inhibit post-operative disc, vertebral body and spinal joint degeneration.

It is yet another object to provide a method of installing the endoprosthesis so as to accurately mate the endoprosthesis with an adjacent specifically formed bone surface. An associated object is to provide an endoprosthesis which will encourage bone attachment to, and growth upon, adjacent outer surfaces of the endoprosthesis.

Yet another object is to provide a vertebral endoprosthesis in which the parts are nononcogenic.

Still another object is to provide a vertebral disc endoprosthesis having a resilient element to accommodate shocks and other forces applied to the spine.

Another object is to provide a highly effective vertebral endoprosthesis which includes several disc endoprostheses and one or more prosthetic vertebral bodies. A related object is to provide these elements in a pre-assembled array for implantation in a patient.

SUMMARY OF THE INVENTION

To accomplish these objects, the invention comprises a resilient body formed of a material varying in stiffness from a relatively stiff exterior portion to a relatively supple central portion. A concaval-convex means at least partly surrounds that resilient body so as to retain the resilient body between adjacent vertebral bodies of a patient's spine. If medical considerations so indicate, several disc endoprostheses can be combined with one or more endoprosthetic vertebral bodies in an entire assembly.

To implant this endoprosthesis assembly, information is obtained regarding the size, shape, and nature of a patient's damaged natural spinal discs. If one or more of the patient's vertebral bodies also require replacement, information about those bodies is also obtained. Thereafter, one or more prosthetic disc units and interposed prosthetic vertebral body units are constructed and preassembled in conformity with that information. Finally, the completed and conformed prosthetic disc and vertebral body assembly is implanted in the patient's spine.

Other objects and advantages of the invention will become apparent upon reading the following detailed description and upon reference to the drawings. Throughout the drawings, like reference numerals refer to like parts.

BRIEF DESCRIPTION OF THE DRAWINGS

FIG. 1 is a fragmentary vertical view of a portion of a human spine in which is installed a novel vertebral disc endoprosthesis embodying the present invention;

FIG. 2 is a fragmentary side elevational view similar to FIG. 1 showing the elements of a patient's spine and having a novel vertebral disc endoprosthesis embodying the present invention installed therein;

FIG. 3 is a sectional view taken substantially in the plane of line 3—3 in FIG. 1;

FIG. 6 is a fragmentary sectional view of a patient's spine similar to FIG. 3 and taken along line 6—6 in FIG. 5, but showing a natural upper vertebral body, and upper endoprosthetic disc; an adjacent endoprosthetic vertebral body; a second or lower endoprosthetic disc; and a second or lower natural vertebral body;

FIG. 7 is a sectional view taken substantially in the plane of line 7—7 of FIG. 6;

FIG. 8 is a fragmentary side elevational view of the assembly shown in FIG. 6; and FIG. 9 is a fragment vertical view, similar to FIG. 1, of a portion of a human spine in which is installed a variant form of the novel vertebral disc endoprosthesis the variant form having a prosthetic longitudinal ligament;

FIG. 10 is a sectional view taken substantially in the plane of line 10—10 in FIG. 9;

DETAILED DESCRIPTION

Figure 4:
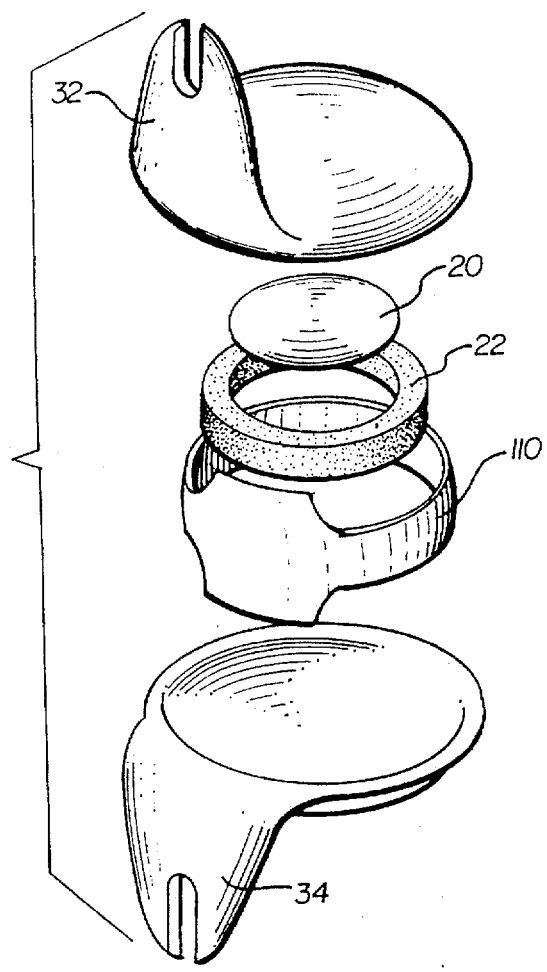
FIG. 4 is an exploded view of the novel vertebral disc endoprosthesis.

While the invention will be described in connection with a preferred embodiment and procedure, it will be understood that it is not intended to limit the invention to this embodiment or procedure. On the contrary, it is intended to cover all alternatives, modifications, and equivalents as may be included within the spirit and scope of the invention as defined by the appended claims.

Turning more specifically to FIGS. 1-3, a portion of a human spine 10 is shown. The illustrated spine 10 has been subjected to a discectomy surgical process. To discourage degeneration of or damage to the natural vertebral bodies 12 and 14 and their respective facet joints, in accordance with the invention, a vertebral disc endoprosthesis 18 is affixed between the adjacent natural vertebral bodies 12 and 14. Here this vertebral disc endoprosthesis 18 comprises a resilient disc body 20 having a relatively stiff annular gasket exterior portion 22 and a relatively supple nuclear central portion 24. The annular gasket 22 can be formed from a suitable biocompatible elastomer of approximately 90 durometer hardness and the nuclear central portion 24 can be formed from a softer biocompatible elastomeric polymer of approximately 30 durometer hardness.

Concaval-convex means 30 surround the resilient body 20 to retain the resilient body 20 between the adjacent natural vertebral bodies 12, 14 in a patient's spine 10. To this end, as shown in FIG. 3, the concaval-convex means 30 comprise two generally L-shaped supports 32 and 34. The supports 32, 34 each have confronting first concaval-convex legs 42, 44, each leg being of relatively constant cross-sectional thickness. Each leg 42, 44 has an outer convex surface 52, 54 for engaging the adjacent bone of the natural vertebral bodies 12, 14. Corresponding inner concave surfaces 62, 64 in confronting array retain the resilient body 20 in its illustrated compressive force shock-absorbing position. These supports 32 and 34 can undergo principle movement away from one another, but only limited secondary translational, rotational and distractional motion will occur. Each support 32, 34 has a second wing or leg 72, 74 extending generally perpendicularly to the first legs 42, 44 respectively, and adapted for affixation to the adjacent bone structure. To carry out aspects of the invention described below, this affixation is effectively accomplished by cannulated screw devices 82, 84 which may be of a biodegradable type manufactured by Zimmer of Largo, Fla. Each device 82, 84 comprises a screw 92, 94; and a screw anchor 102, 104 adapted to threadably receive the screw extends radially into and seats within the bone structure 12, 14 as especially shown in FIG. 3.

To discourage and prohibit migration of fluids between the endoprosthesis 18 and adjacent parts of the anatomy, a seal member 110 is attached to the supports 32, 34 so as to surround the resilient body 20 comprised of the gasket 22 and nucleus 24, in accordance with another aspect of the invention. Here, this seal member 110 comprises a flexible sheet material having a multiplicity of pores. Preferably, the pores are from about 5 microns to about 60 microns in size. A flexible, strong polymer sheet material from which this seal is formed can be a Kevlar-like material, or it can be Goretex-like material, or other appropriate biocompatible material, such as polyether, polyurethane, or polycarbonate urethane membranes, can be used. Kevlar material is offered by the E. I. DuPont de Nemours Company of Wilmington, Del. and Goretex material is offered by the W. T. Gore Company of Flagstaff and Phoenix, Ariz. Known sealing material can be applied to the flexible sheet material so as to render the flexible sheet material substantially impervious to the passage of any fluid. A watertight seal is perfected when the seal 110 is glued or otherwise affixed to the legs 42, 44 and mediate portions of the legs 72, 74 as suggested in FIGS. 1-3.

Figure 11:
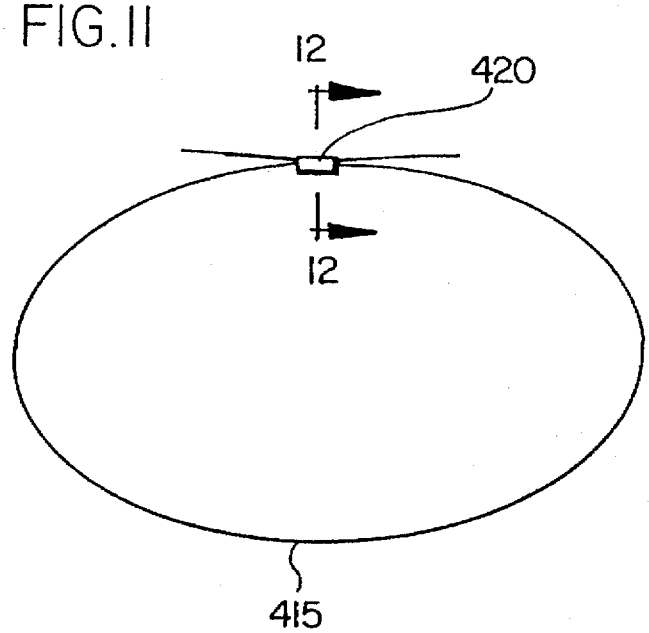
FIG. 11 is a top view of a retainer means for use with a vertebral disc endoprosthesis.
Figure 12:
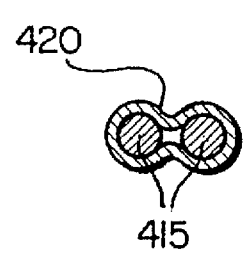
FIG. 12 is a sectional view taken substantially in the plane of line 12—12 of FIG. 11.
Figure 13:
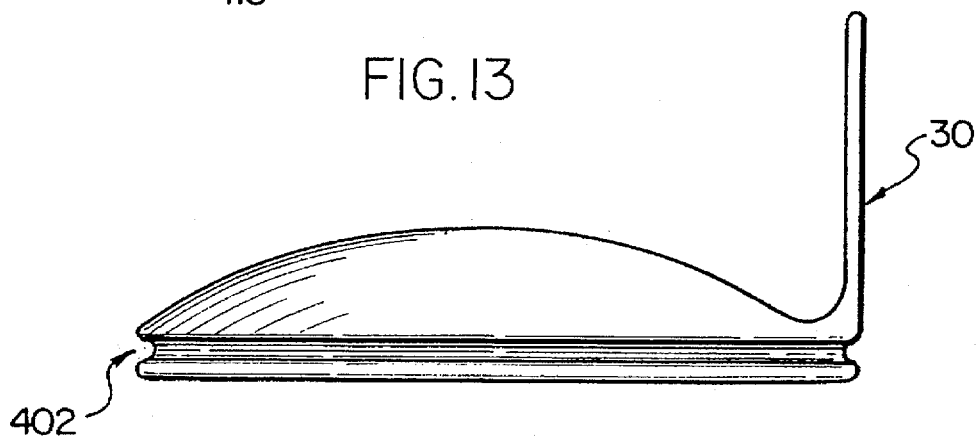
FIG. 13 is a side view of a vertebral disc endoprosthesis having a groove for receiving the retainer means.
Figure 14:
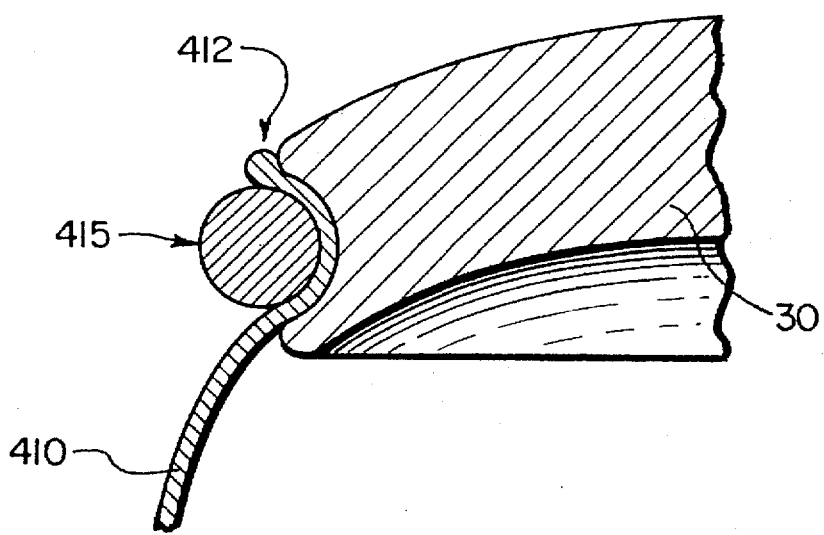
FIG. 14 is a cross-sectional view of the retainer means in use.

In an alternative embodiment, the watertight seal between the endoprosthesis 18 and adjacent parts of the anatomy can be provided by developing a groove 402 completely encircling the periphery of each of the legs 42, 44. Only one of the grooves is shown in FIG. 13. In this embodiment, the seal member 410 is provided with a beaded edge 412 for each groove. Additionally, a retaining band 415 is provided for each groove to retain the seal member 410 in grooves 402. The retaining bands 415 can be in the form of a biocompatible monofilament wire of, for example, stainless steel or titanium, a synthetic polymer cable or a braided wire cable. As shown in FIG. 11, each retaining band is crimped anteriorly by a crimping sleeve 420. Of course, more than one crimping sleeve may be used, if necessary. Although one sealing arrangement consisting of the groove, beaded edge and retaining band is shown in FIG. 14, it should be understood that the sealing arrangement on the concaval-convex leg of the other support is identical in design and function.

In use, the seal member 410 is placed about the concaval-convex means 30. The retaining bands 415 are then placed adjacent to the respective groove 402 and crimped anteriorly, thereby fitting the bands into the grooves. Each beaded edge 412 prevents the slipping of the seal member underneath the retaining band. Thus, the retaining band, the groove and the beaded edge all cooperate to provide a water-tight seal to prevent the migration of fluids between the endoprosthesis 18 and adjacent parts of the anatomy. Glue can also be used to affix the seal member to the concaval-convex means 30 as a supplemental means for perfecting the seal.

In accordance with another aspect of the invention, the supports 32, 34 are formed of a biocompatible metal which may contain chromium cobalt or titanium. Surface roughening or titanium beading 112, 114 on the exterior surfaces 52, 54 of legs 42, 44 encourages positive bonding between the adjacent bone and the convex surfaces 52, 54.

As suggested in FIGS. 9 and 10, a prosthetic longitudinal ligament 250 can be connected between the screws 92, 94 to limit motions between elements of the spine 10 in the area where the endoprosthesis 18 is implanted. This strap 250 may be made of the Kevlar-like material or the Goretex-like material described above, or it may be made of any other strong biocompatible material.

Figure 5:
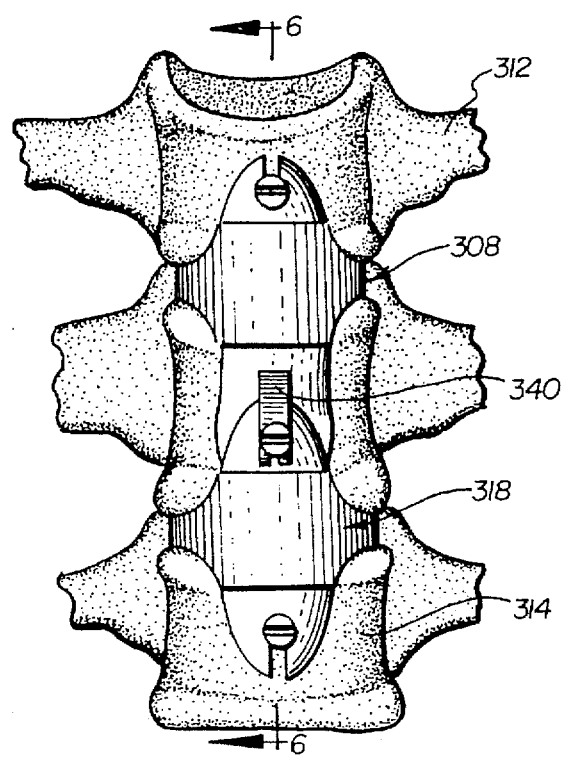
FIG. 5 is a vertical fragmentary view of a patient's spine similar to FIG. 1, but showing a series of novel disc endoprosthesis units installed in the spine and interconnected to one another.

In accordance with another aspect of the invention, multiple endoprosthetic disc units can be placed in series with a straddling interlock appendage providing stability and fixation as shown in FIG. 5. Entire portions of a patient's spine can be replaced by a series of interconnected endoprosthetic vertebral bodies and endoprosthetic disc units. FIGS. 6–8 show an upper natural vertebral body unit 312 to which an upper endoprosthetic body 308 has been attached. A lower natural vertebral body 314 has attached, at its upper end, an endoprosthetic disc unit 318. Between these endoprosthetic disc units 308 and 318 is an endoprosthetic vertebral body 320. As suggested by FIG. 7, the endoprosthetic vertebral body 320 need not be irregularly shaped in cross sectional aspect; rather, manufacturing processes may suggest that it have a circular cross-sectional shape. As show in FIGS. 6 and 8, this endoprosthetic vertebral body 320 comprises a titanium element 321, to which are attached the preformed upper and lower endoprosthetic vertebral body upper and lower concaval-convex elements 322, 324. Each concaval-convex element 322, 324 is attached to the prosthetic vertebral body 320, as shown in FIG. 7, by extending set screws 330 through the titanium vertebral body 321 into a stem-like projection 331 extending from each of the concaval-convex elements 322, 324. A hole 360 in the body 320 accommodates the stem-like projections 331 of the concaval-convex elements 322 and 324. The stem-like projection 331 of the concaval-convex elements 322 and 324 is used only in conjunction with a prosthetic vertebral body implant construction 320.

An ear 340 is affixed, as by weldments 341, to a leg 342 extending from a concaval-convex element 322 as illustrated in FIGS. 6 and 8. An anchor 352 can be threaded into the endoprosthetic vertebral body 320, and a screw 362 can be turned into the anchor 352 so as to rigidly assemble the leg 342 to a leg 354 extending from the lower endoprosthetic disc unit 318.

The upper disc endoprosthesis 308, the endoprosthetic vertebral body 320, and the lower disc endoprosthesis 318 can all be assembled and interconnected as a unit before implantation in a patient's body when indicated.

As also suggested in FIG. 6, the annular corners 372, 374 of natural vertebral bodies 312, 314 each can extend irregularly radially outwardly of the adjacent disc endoprosthesis 308, 318. However, the corners 382B, 384B of the prosthetic vertebral body 320 do not generally extend significantly outside those disc units 308, 318, thus discouraging vertebral body engagement with and consequent abrasion or other damage to adjacent portions of the patient's natural anatomy. Preferably the endoprosthetic vertebral body 320 is not exactly right cylindrical in shape, but is rather slightly biconical; that is, the endoprosthetic vertebral body 320 has a waist 390 of minimum radius R at an axial medial point as suggested in FIG. 6.

According to yet another aspect of the invention, novel surgical procedures permit effective and permanent installation of the endoprosthetic vertebral body 320 and associated parts. First, a surgeon or medical technician develops information about the size, shape and nature of a patient's damaged vertebral body or bodies from radiographs, CT and/or MRI scans, noting specifically the anterior-posterior and lateral dimensions of the end plate of each involved vertebral body and the vertical height of the anterior aspect of each involved vertebral and/or proximate vertebral body and vertical height of the mid portion of involved and proximate relatively normal intervertebral disc spaces. This information is transmitted by telephone, computer datalink or documentary transport to a specialized laboratory. That laboratory constructs one or more prosthetic assemblies of the sort shown in FIG. 6 in conformity with the received information and this disclosure. Each of the assemblies can include a prosthetic vertebral body 321, and at each body end is a prosthetic disc 308, 318. Each prosthetic disc unit comprises, in turn, the concaval-convex elements 30; the resilient body 20 interposed between the concaval-convex elements; and the seal unit 110 secured around the interior legs and resilient body. Thereafter, the completed and conformed assembly is implanted in the patient's spine 10.

When the unit or units have been received and the patient properly prepared, the damaged natural spinal disc or discs and vertebral body or bodies are removed and the adjacent spinal bone surfaces are milled or otherwise formed to provide concave surfaces to receive the confronting convex surfaces 52, 54. Thereafter, the disc units and vertebral body are installed in the patient's spine.

To accurately locate the concaval-convex surfaces in the patient's spine, holes 382A, 384A (FIG. 3) are precisely located and then formed in the bone structure using a measuring instrument centered in the evacuated natural intravertebral disc space. These holes are then tapped to form female threads therein. When the threads have been formed, the anchors 102, 104 are implanted in the respective tapped holes, thereby creating an imaginary platform of reference points located precisely with respect to the patient's spine. After the holes have been formed and the anchors 102, 104 implanted, a bone surface milling jig (not shown) is affixed to the anchors 102, 104 and the desired concave surfaces of predetermined shape are formed on the inferior and superior surfaces of the opposing vertebral bodies using one of a selection of predetermined milling head or bit sizes. Thereafter, the bone milling jig is removed and the concaval-convex elements 52, 54 identical in shape to the milled surfaces 112, 114 are inserted between the distracted milled vertebral bodies 12, 14. The distraction device is then moved. The concaval-convex structures are then attached by the same anchors 102, 104 to the bone, thus insuring a precise and stable mate between the bone surfaces and the convex surfaces 52, 54.

If necessary, a damaged implanted nucleus and/or gasket 24 can be removed and replaced. This can be accomplished by slitting the seal 110; removing the annular gasket 24 and damaged nucleus 22, and replacing them with new, undamaged elements. Thereafter, the seal 110 can be re-established by suturing or gluing closed the slit seal.

We claim:

1. A vertebral disc endoprosthesis, comprising a resilient body formed of materials varying in stiffness from a relatively stiff exterior portion to a relatively supple central portion; and concaval-convex elements at least partly surrounding the resilient body between adjacent vertebral bodies for retaining the resilient body between adjacent vertebral bodies in a patient's spine, and wherein said concaval-convex elements each comprise generally L-shaped supports, each support having a first concaval-convex leg, the first leg having an outer convex surface for engaging adjacent bone and a corresponding inner concave surface for retaining the resilient body, each support further having a second leg extending generally perpendicularly to the first leg and adapted for affixation to adjacent bone structure.

2. A vertebral disc endoprosthesis according to claim 1 wherein said resilient body comprises an annular gasket and a nuclear central portion.

3. A vertebral disc endoprosthesis according to claim 1 further comprising cannulated screw means for attaching the concaval-convex element supports to adjacent bone structure.

4. A vertebral disc endoprosthesis according to claim 3 wherein said cannulated screw means comprises a screw, and a screw anchor seatable within bone structure and adapted to threadably receive the screw.

5. A vertebral disc endoprosthesis according to claim 1 further comprising a seal member attached to the concaval-convex elements and surrounding said resilient body.

6. A vertebral disc endoprosthesis according to claim 5 wherein said seal member comprises a flexible shell material having a multiplicity of pores, the pores being from about 5 microns to about 60 microns in size.

7. A vertebral disc endoprosthesis according to claim 6 further including sealing means applied to said flexible sheet material to render said flexible sheet material substantially impervious to the passage of any fluid.

8. A vertebral disc endoprosthesis according to claim 5 wherein said concaval-convex elements and said seal member collectively surround said resilient body with a watertight seal.

9. A vertebral disc endoprosthesis according to claim 2 wherein said annular gasket is relatively stiff and said nuclear central portion is relatively supple.

10. A vertebral disc endoprosthesis according to claim 1 wherein said concaval-convex elements are formed of a biocompatible metal.

11. A vertebral disc endoprosthesis according to claim 1 wherein said concaval-convex elements are formed of a metal containing titanium.

12. A vertebral disc endoprosthesis according to claim 1 wherein said concaval-convex elements are formed of a metal containing chromium cobalt.

13. A vertebral disc endoprosthesis according to claim 10 wherein said concaval-convex elements are each partly defined by exterior surfaces, and wherein the endoprosthesis further includes metal beading on at least part of the exterior concaval-convex element surfaces for encouraging bonding between bone and said exterior concaval-convex element surfaces.

14. A vertebral disc endoprosthesis according to claim 1 wherein said concaval-convex elements are provided with roughened outer surfaces to encourage positive bonding of bone to said concaval-convex element surfaces.

15. A vertebral disc endoprosthesis according to claim 1 wherein said concaval-convex elements are formed of a non-oncogenic material.

16. The vertebral disc endoprosthesis according to claim 1 wherein each concaval-convex element is provided with a respective groove.

17. The vertebral disc endoprosthesis according to claim 16 further comprising a seal member including beaded edges, the seal member attached to the concaval-convex elements and surrounding said resilient body.

18. The vertebral disc endoprosthesis according to claim 17 further comprising retainer means for retaining the seal member against said grooves, the retainer means cooperating with the beaded edges and the grooves to form a watertight seal.

19. The vertebral disc endoprosthesis according to claim 18 wherein the retainer means can be in one of the following forms: a biocompatible monofilament metal wire, a synthetic polymer band or a braided wire cable.

20. The vertebral disc endoprosthesis according to claim 19 wherein the biocompatible monofilament metal wire is formed of stainless steel or titanium.

21. The vertebral disc endoprosthesis according to claim 18 further comprising a crimping means for crimping the retainer means about the seal member.

22. The vertebral disc endoprosthesis according to claim 1 wherein each support includes a groove about its circumference, the groove encircling the periphery of the first leg.

23. A vertebral endoprosthesis comprising an integral disc unit, said unit including a pair of confronting L-shaped supports having concaval-convex shapes in given legs, a resilient body interposed between the supports, and a flexible seal extending from one support to the other and sealing the resilient body within the supports inside a substantially watertight compartment.

24. A vertebral endoprosthesis according to claim 23 further comprising a plurality of said integral disc units.

25. The vertebral endoprosthesis according to claim 23 wherein each support includes a groove about its periphery and wherein the seal includes beaded edges.

26. The vertebral endoprosthesis according to claim 25 further comprising retainer means for retaining the seal against said grooves, the retainer means cooperating with the beaded edges and the grooves to form a watertight seal.

27. The vertebral endoprosthesis according to claim 26 wherein the retainer means can be in one of the following forms: a biocompatible monofilament metal wire, a synthetic polymer band or a braided wire cable.

28. The vertebral endoprosthesis according to claim 27 wherein the biocompatible monofilament metal wire is formed of stainless steel or titanium.

29. The vertebral endoprosthesis according to claim 26 further comprising a crimping means for crimping the retainer means about the seal.

30. A vertebral disc endoprosthesis comprising a resilient nucleus, rigid concaval-convex elements at least partly surrounding the nucleus, an annular gasket ring surrounding the nucleus, and a seal member formed of flexible material and attached to the concaval-convex elements and surrounding the nucleus and the annular gasket ring.

31. A vertebral disc endoprosthesis according to claim 30 wherein said concaval-convex elements each comprise generally L-shaped supports, each support having a first concaval-convex leg, the first leg having an outer convex surface for engaging adjacent bone and a corresponding inner concave surface for retaining the nucleus, each support further having a second leg extending generally perpendicularly to the first leg and adapted for affixation to adjacent bone structure.

32. A vertebral disc endoprosthesis, according to claim 31 further including screw means adapted for connection to said legs and for affixation in a generally radial direction in adjacent generally cylindrical bone vertebrae.

33. The vertebral disc endoprosthesis according to claim 31 wherein each support includes a groove about its circumference.

34. A vertebral disc endoprosthesis according to claim 30 further including means affixed to the concaval-convex elements for encouraging bone growth partially upon and bone bonding with said concaval-convex elements.

35. A vertebral disc endoprosthesis according to claim 30 further including means for interconnecting one of said concaval-convex elements to a concaval-convex element of another vertebral disc endoprosthesis, thereby permitting the replacement of several natural vertebral discs.

36. The vertebral disc endoprosthesis according to claim 30 wherein each element includes a respective groove and wherein the seal member includes beaded edges.

37. The vertebral disc endoprosthesis according to claim 36 further comprising retainer means for retaining the seal member against said grooves, the retainer means cooperating with the beaded edges and the grooves to form a watertight seal.

38. The vertebral disc endoprosthesis according to claim 37 wherein the retainer means can be in one of the following forms: a biocompatible monofilament metal wire, a synthetic polymer band or a braided wire cable.

39. The vertebral disc endoprosthesis according to claim 38 wherein the biocompatible monofilament metal wire is formed of stainless steel or titanium.

40. The vertebral disc endoprosthesis according to claim 37 further comprising a crimping means for crimping the retainer means about the seal member.

41. A vertebral disc endoprosthesis comprising a resilient nucleus, first and second rigid concaval-convex elements at least partly surrounding the nucleus, first and second legs formed, respectively, with the first and second rigid concaval-convex elements, first and second means for affixing the respective legs to vertebral bodies adjacent the concaval-convex elements and nucleus, and longitudinal ligament prosthesis means extending between the legs of the first and second concaval-convex elements to inhibit undesirable motion of the vertebral bodies relative to one another.

42. A vertebral disc endoprosthesis comprising a rounded, resilient nucleus body convex on all surfaces and concaval-convex elements, each concaval-convex element being of relatively constant cross-sectional thickness and having an outer convex surface for engaging adjacent bone structure which has been milled to mate with the concaval-convex element outer convex surface, and a corresponding inner concave surface for engaging the rounded resilient body, wherein said resilient nucleus body comprises a relatively resilient central body and a relatively stiff gasket surrounding a circumference of the central body, the resilient nucleus body snugly engaging the adjacent, mating concave surfaces of the concaval-convex elements.

43. A vertebral disc endoprosthesis according to claim 42 wherein the concaval-convex elements do not engage one another.

* * * * *